United States Patent [19]

Seiden et al.

[11] 3,968,169

[45] July 6, 1976

[54] PROCESS FOR PREPARING POLYBLYCEROL

[75] Inventors: Paul Seiden, Cincinnati; James Bruce Martin, Hamilton, both of Ohio

[73] Assignee: The Procter & Gamble Company, Cincinnati, Ohio

[22] Filed: Jan. 20, 1975

[21] Appl. No.: 542,471

Related U.S. Application Data

[63] Continuation-in-part of Ser. No. 420,728, Nov. 30, 1973, abandoned.

[52] U.S. Cl. ............................ 260/615 R; 260/338
[51] Int. Cl.² ........................................ C07C 41/10
[58] Field of Search .............................. 260/615 R

[56] References Cited
UNITED STATES PATENTS 2,110,695   3/1938   Batchelder ..................... 260/615 R
2,182,397   12/1939   Eckey .............................. 260/615 R

*Primary Examiner*—Howard T. Mars
*Attorney, Agent, or Firm*—Ronald L. Hofer

[57] ABSTRACT

A process for preparing polyglycerol by heating glycerol under reduced pressure in the presence of a catalytic quantity of sulfuric acid and a low molecular weight glyceride until from about 25 to about 75 percent of the glycerol is polymerized. The condensation is terminated by inactivating the catalyst by adding a substantially stoichiometric amount of a suitable neutralizing agent. Unreacted glycerol and cyclic diglycerol are removed by distillation. The polyglycerol so prepared can advantageously be employed in the preparation of polyglycerol fatty acid esters which are excellent food emulsifiers.

7 Claims, No Drawings

3,968,169

PROCESS FOR PREPARING POLYBLYCEROL

CROSS REFERENCE TO RELATED APPLICATION

This application is a continuation-in-part application of application, Ser. No. 420,728, filed Nov. 30, 1973, now abandoned, and entitled "Process for Preparing Polyglycerol."

BACKGROUND OF THE INVENTION

This invention relates to a process for preparing polyglycerol. In more detail there is provided a process for preparing polyglycerol by treating glycerol under well-defined conditions of temperature and pressure in the presence of a catalytic amount of a system of adjuvants capable of promoting the polymerization reaction. The adjuvant system comprises sulfuric acid and a lower aliphatic acid ester of glycerol. When from about 25 to about 75 percent of the glycerol is polymerized, the glycerol polymerization is terminated by inactivation of the adjuvant system. This can be done by neutralizing the adjuvants with a substantially stoichiometric amount of a neutralizing agent. Unreacted glycerol and cyclic diglycerol are then removed by distillation. The polyglycerol mixture so prepared contains a high percentage of linear di- and triglycerols and a low percentage of polyglycerols comprising seven or more glycerol units. The polyglycerol mixture can be esterified with a fatty acid in known manner to provide polyglycerol fatty acid esters having a polyglycerol distribution which is substantially similar to that of the polyglycerol prior to esterification. These esters are particularly suitable for use as emulsifiers in food applications.

Polyglycerols and the corresponding esters of these polyglycerols and higher fatty acids are known food additives, especially emulsifiers, and also have been used for various food applications. For example, polyglycerol fatty acid esters have been used as anti-spattering agents in cooking and salad oils as disclosed in U.S. Pat. Nos. 3,415,658 and 3,415,659. U.S. Pat. No. 3,528,823 relates to a fluid shortening containing a polyglycerol fatty acid ester emulsifier.

It is known that polyglycerol fatty acid esters can be prepared by polymerizing glycerol in the presence of an alkaline or acid condensation catalyst. The esterification of the polyglycerols so prepared with fatty acids in the presence of an esterification catalyst is also known. The catalytic polymerization of glycerol to polyglycerol is, for instance, described in U.S. Pat. No. 2,487,208 to Alsop. The polymerization is carried out under atmospheric pressure at an elevated temperature, for example, from 200°C to 280°C. Alkali metal and alkaline earth metal compound condensation catalysts can be used. Canadian Pat. No. 834,214 to Kurt et al. discloses the preparation of monoesters of polyglycerol and fatty acids whereby the alkaline condensation catalyst employed is not merely deactivated, but is essentially completely removed from the condensation reaction mixture prior to esterification. For that purpose, the condensation reaction mixture is contacted with both anionic and cationic exchange resins.

U.S. Pat. No. 2,182,397 to Eckey relates to a process for forming ether derivatives of polyhydric alcohols including derivatives that contain esterified fatty acid groups. The polyhydric alcohol, e.g. glycerol, is partially esterified with a carboxylic acid containing two or more carbon atoms. The etherification (polymerization) is carried out in presence of a water carrier and an esterifying catalyst such as sulfuric acid and certain aromatic sulfonic acids. It is also mentioned that the acid catalyst can be neutralized.

While the art is crowded and diverse, it fails to recognize that polyglycerol mixtures having a particular distribution of highly functional emulsifier precursors can be prepared by polymerization of glycerol in the presence of adjuvants capable of controlling the polymerization reaction. It has been disclosed that the neutralization of an alkaline condensation catalyst is deficient as presumably traces of the alkaline material escape neutralization and accordingly are present during the subsequent esterification reaction. The continued polymerization of glycerol and lower polyglycerols to higher polyglycerols is thereby promoted. It is observed that in polymerizing glycerol in the presence of an alkaline catalyst, acid by-products are formed. During the condensation process these by-products react with the alkaline catalyst to form organic salts which cannot be easily deactivated or removed and which act as condensation and interesterification catalysts.

It is an object of this invention to provide a process for preparing polyglycerol compositions which can advantageously be used for the preparation of highly functional polyglycerol fatty acid esters.

It is an additional object of this invention to provide a process for preparing polyglycerol compositions containing a high percentage of lower polyglycerols and a low percentage of polyglycerols comprising seven or more glycerol units.

Other objects of the invention will become apparent from the description of the invention provided hereinafter.

SUMMARY OF THE INVENTION

The present invention is based in part upon the discovery that particular polyglycerol compositions capable upon simple esterification of providing highly functional emulsifiers can be prepared by adhering to certain polymerization process conditions described hereinafter. This process comprises heating glycerol under reduced pressure in the presence of a catalytic amount of adjuvants capable of promoting the glycerol polymerization until a given level of glycerol has polymerized. The condensation reaction is then terminated by inactivating the catalyst through the addition of a substantially stoichiometric amount of a suitable neutralizing agent. Unreacted glycerol and cyclic diglycerol are subsequently removed by distillation. The polyglycerol so prepared can be esterified with a fatty acid to provide a polyglycerol fatty acid ester which can advantageously be used as an emulsifier ingredient in food applications.

DETAILED DESCRIPTION OF THE INVENTION

This invention relates to a process for preparing polyglycerol, comprising; (1) heating glycerol under a given set of conditions in the presence of an adjuvant system capable of promoting the polymerization reaction; (2) deactivating the adjuvants by the addition of a substantially stoichiometric amount of a suitable neutralizing agent; and (3) distilling off unreacted glycerol. Each of these essential steps is discussed in detail hereinafter.

In the first step, glycerol is heated to a temperature from about 110° to about 180°C, preferably from about 120°C to about 145°C under a pressure below about 400 mm, preferably from about 1 mm to about 20 mm absolute mercury pressure. The glycerol condensation is carried out in the presence of an adjuvant system comprising from about 0.03 to about 3% by weight, preferably from about 0.08 to about 0.3% by weight of sulfuric acid; and from about 0.1 to about 10% by weight, preferably from about 0.5 to about 5% by weight, of a glyceride having the formula:

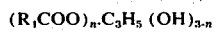

wherein $R_1$ represents $CH_3-$, or $CH_3CH_2-$, and $n$ represents an integer from 1 to 3 inclusive. The polymerization is conducted until from about 25 to about 75 percent, preferably from about 35 to about 60 percent, of the glycerol is polymerized.

The condensation (polymerization) temperature is in the range of from about 110° to about 180°C. Heating the reaction mixture to a temperature below about 110°C results in some glycerol polymerization; however, the reaction speed is insufficient to be of practical interest. Carrying out the condensation reaction at a temperature above about 180°C can result in the formation of a polyglycerol having an undesirable color and odor.

The condensation reaction is carried out under a pressure below about 400 mm, preferably in the range from about 1 mm to about 20 mm absolute mercury pressure. Glycerol polymerization at a high pressure tends to be too slow.

The adjuvant system comprises sulfuric acid and a lower carboxylic acid ester of glycerol. The latter is represented by the esterification product of glycerol with acetic or propionic acid. Mixed esters can also be used. Highly preferred for use herein are mono-, di-, and tri-acetin. It will be appreciated that the glyceride can also be prepared in situ from its precursors, i.e. acetic or propionic anhydride and glycerol.

The glycerol condensation is catalyzed by the addition of sulfuric acid and a particular glycerol ester in the quantities defined hereinabove. The minimum amounts of sulfuric acid (0.03%) and glyceride (0.1%) are needed to noticeably perceive the advantages of the claimed process. Using more than 3% of sulfuric acid can contribute, particularly towards the end of the condensation reaction, to charring of organic material and to the inherent formation of undesirable by-products. Using more than 10% of the glyceride can, as a result of interesterification, contribute to the formation of low molecular weight carboxylic acid esters of polyglycerol. These latter compounds can adversely affect the emulsifying properties of the polyglycerol fatty acid esters.

The glycerol condensation is terminated when from about 25 to about 75 percent, preferably from about 35 to about 60% by weight of the glycerol is polymerized. The endpoint of the condensation is determined by means of refractometer index readings (Butyro scale at 60°C) as described in "OFFICIAL METHODS OF ANALYSIS OF THE ASSOCIATION OF OFFICIAL AGRICULTURAL CHEMISTS," ninth edition, 1960; published by Association of Official Agricultural Chemists, Washington, D.C., page 359. Apparently, in the glycerol polymerization process the initial rate of diglycerol formation is higher than that of the longer chain polymers. The diglycerol content reaches its maximum concentration when about 50 percent of the glycerol has been polymerized. From that point onwards, the rate of diglycerol formation is lower than the rate at which diglycerol is further polymerized. Accordingly, the concentration of diglycerol decreases. Thus, a high polymerization completeness is proportional to a broad polymer species distribution. This, in turn, is useful as the concentration of the lower polyglycerol can, to a certain extent, be varied by terminating the condensation reaction at more or less advanced level of glycerol condensation within the claimed range.

During the condensation gas, preferably nitrogen, sparging and/or mechanical agitation is normally applied.

As used in the specification and claims herein, the terms "polyglycerol" and "polyglycerol mixture" are employed interchangeably and refer to a mixture of compounds which comprises a mixture of glycerol, diglycerol and homologous polyglycerol molecules. The terms (glycerol) "polymerization" and "condensation" are used interchangeably to define the reaction resulting in the etherification of two or more molecules of glycerol under formation of water. The terms "adjuvants(s)", "adjuvant system" and "catalyst" are also used interchangeably to define the function of the combination of the sulfuric acid and the glycerol derivative as being to modify or increase the rate of glycerol polymerization in a catalytic manner, i.e., without undergoing substantial chemical changes during the condensation reaction.

When the desired degree of glycerol condensation is attained, the polymerization is terminated by neutralizing the catalyst, i.e. essentially the sulfuric acid, with a substantially stoichiometric amount of a suitable neutralizing agent. The neutralizing agent can be represented by all ingredients which are known to be suitable for neutralizing sulfuric acid. Suitable neutralizing agents include, by way of example, alkali metal and alkaline earth metal hydroxides, carbonates, and bicarbonates such as sodium hydroxide, potassium hydroxide, lithium hydroxide, barium hydroxide, calcium hydroxide, sodium carbonate, sodium bicarbonate, potassium bicarbonate, calcium oxide, and the like. This enumeration is not intended to be limiting as other neutralizing agents can be employed. It may be desirable to cool the reaction mixture during neutralization, particularly when the level of sulfuric acid present is above about 1%. This eliminates the danger of overheating which can deteriorate the reaction mixture (color and odor) because of excessive neutralization heat.

Following the inactivation (neutralization) of the catalyst, the unreacted glycerol and the largest part of the cyclic diglycerol are distilled off by (fractional) distillation. This is normally done at a temperature in the range from about 150° to about 300°C at a pressure below about 400 mm, preferably in the range from about 1 to about 20 mm absolute mercury pressure. This set of distillation conditions represents a practical optimization for the purpose of removing the undesired glycerol without adversely affecting the overall quality, particularly color and odor, and emulsifying properties of, for example, the polyglycerol fatty acid ester prepared from the polyglycerol made by the claimed process.

It will be appreciated that the polyglycerol distribution of the corresponding polyglycerol fatty acid esters is critical to the attainment of superior emulsifying properties in food applications. Polyglycerol esters known in the art and containing less than 25 percent of the di- and triglycerol esters are unsatisfactory from the standpoint of providing acceptable emulsifying properties to shortenings. Similarly, polyglycerol esters containing high levels, e.g. more than 15 percent, of mono- and diglycerides (mono- and diesters of glycerine) or long-chain (more than 7 glycerol units) polyglycerol esters are not suitable for producing superior food applications. The presence of mono- and diglycerides is detrimental to the performance of polyglycerol esters in most food applications. While the detrimental effect of the β-tending diglycerides is instantaneous, the effect of monoglycerides is slower and shows up more gradually upon aging. Mono- and diglycerides can be present in polyglycerol esters as a result of contamination. Thus, the polymerization completeness of glycerol to polyglycerol will affect the amount of glycerine present in the polyglycerol and available for the formation of mono- and diglycerides in a subsequent esterification reaction. As pointed out before, a complete conversion of glycerol to polyglycerol will provide high levels of long-chain polyglycerols such as hexa-, hepta-, and octaglycerols. However, these long-chain polyglycerols yield monoesters which are neither fat-soluble nor functional emulsifiers. In view of the unsatisfactory emulsifying properties of polyglycerol esters containing mono- and diglycerides, esters of so-called "average" hexa and higher polyglycerols have been preferred for food applications because they contain only minor amounts of mono- and diglycerides. After the unreacted glycerol and (part of) the cyclic diglycerol are removed, the remaining polyglycerol mixture contains a high level of lower (di- and tri-) polyglycerols and a low level of polyglycerols containing 7 or more glycerol units. The polyglycerol can then be esterified with a fatty acid or a mixture of fatty acid to provide food emulsifiers. Examples of these polyglycerol fatty acid emulsifiers and their use in food technology are described in the following U.S. Patent Applications:

1. Liquid Pumpable Shortening, inventors Paul Seiden and John R. Shaffer, Ser. No. 420,731, filed Nov. 30, 1973, now abandoned;
2. Dry Culinary Cake Mix, inventor Paul Seiden, Ser. No. 420,729, filed Nov. 30, 1973, now abandoned; and
3. All Purpose Liquid Shortening Compositions, inventor Paul Seiden, Ser. No. 420,730, filed Nov. 30, 1973, now abandoned.

It can be desirable to additionally tailor the polyglycerol composition described hereinbefore. The term "tailor" is meant to express that the length of the polyglycerol chain, which is used for preparing the corresponding emulsifier ester, can be varied for specific (tailor-made) applications. For example, the above polyglycerol composition can be distilled from about 235° to about 255°C at 5 mm absolute mercury pressure to fractionate the linear diglycerol in combination with a minor amount of glycerol. The latter is then removed in a separate distillation step.

The polyglycerol compositions herein can be esterified or interesterified with fatty acid to provide highly functional polyglycerol ester emulsifiers. When the polyglycerol is to be used, after esterification, as a food emulsifier, it is desirable that the polyglycerol ester be substantially free of odor and also have a bland taste. For that purpose, the polyglycerol ester is preferably deodorized. Composition alterations can occur, which frequently can lead to a loss of functionality, if the deodorization is carried out on the polyglycerol ester alone or in combination with a shortening. These alterations can be conveniently avoided by carrying out the deodorization process in the presence of an excess polyglycerol, preferably immediately after the esterification reaction is completed. The deodorization is preferably carried out at the same temperature as the esterification reaction.

The following examples demonstrate the invention and facilitate its understanding.

EXAMPLE I

Four hundred sixty six pounds glycerol, 11.95 pounds technical grade monoacetin and 239 grams sulfuric acid are charged to a stainless steel reactor equipped with a nitrogen sparging ring and mechanical agitation. The glycerol polymerization is carried out at 270°F (about 132°C) and 5 mm absolute mercury pressure. The polymerization reaction is terminated through the addition of 180 grams sodium hydroxide when the refractive index reaches 72.7 (at 60°C on the Butyro scale). At this stage 54.8 percent of the glycerol is polymerized. The composition of the reaction mixture at certain refractive indexes can be seen from the following Table:

| Refractive Index (Butyro Scale: 60°C) | | 66.6 | 70.1 | 71.0 | 72.7 |
|---|---|---|---|---|---|
| Glycerol | % | 58.9 | 52.4 | 48.2 | 45.2 |
| Linear diglycerol | % | 24.4 | 27.7 | 28.7 | 29.1 |
| Cyclic diglycerol | % | 1.7 | 1.7 | 1.8 | 2.5 |
| Linear triglycerol | % | 8.8 | 10.4 | 11.0 | 12.0 |
| Cyclic triglycerol | % | 1.2 | 1.2 | 1.4 | 1.6 |
| Linear tetraglycerol | % | 3.2 | 4.0 | 5.6 | 6.0 |
| Linear pentaglycerol | % | 1.2 | 1.6 | 2.1 | 2.2 |
| Hexaglycerol | % | 0.6 | 1.0 | 1.2 | 1.4 |

The glycerol and cyclic diglycerol are then distilled off at temperatures from 300°F to 400°F (about 149°C to 204°C) and 5 mm absolute mercury pressure. The distillation is monitored by refractive index control. When the refractive index attains 87.5 the distillation is completed. The polyglycerol so produced has the following composition:

| Component | Polyglycerol Compositions in % By Weight |
|---|---|
| Glycerol | 2.3 |
| Linear diglycerol | 55.2 |
| Cyclic diglycerol | 0.5 |
| Linear triglycerol | 22.1 |
| Cyclic triglycerol | 1.4 |
| Linear tetraglycerol | 9.2 |
| Cyclic tetraglycerol | 1.2 |
| Linear pentaglycerol | 5.2 |
| Hexaglycerol | 1.8 |
| Heptaglycerol | 0.6 |
| Glycerol of more than seven glycerol units; organic and inorganic salts; polymerization by-products; moisture | —Balance to 100— |

Eighty pounds of the above polyglycerol composition is esterified in a known manner with 55 pounds of food grade stearic acid. The polyglycerol fatty ester obtained exhibits outstanding emulsifying properties when used in cakes and fluid shortenings.

EXAMPLE II

The polyglycerol composition of Example I is additionally tailored. 165 pounds of that particular polyglycerol is charged to a stainless steel reactor equipped with a nitrogen sparging ring, steam and electrical heating devices, mechanical agitation, condensers, receivers and vacuum outlets. The polyglycerol is gradually heated from 470°F to 515°F (about 243°C to 268°C) under 5 mm absolute mercury pressure whereby the linear diglycerol and the remaining glycerol are distilled off. The operation is discontinued when 83 pounds is collected. To remove the minor amount of glycerol from the distillate, the latter is recharged to the stainless steel reactor and maintained at about 440°F (about 227°C) under 5 mm absolute mercury pressure for about one hour. The remaining linear diglycerol has the following composition:

| Component | Polyglycerol Compositions In % By Weight |
|---|---|
| Glycerol | Trace |
| Linear diglycerol | 85.1 |
| Cyclic diglycerol | 0.2 |
| Linear triglycerol | 6.6 |
| Cyclic triglycerol | 2.3 |
| Linear tetraglycerol | 4.5 |
| Cyclic tetraglycerol | 0.1 |
| Linear pentaglycerol | 0.6 |
| Glycerol of more than seven glycerol units; organic and inorganic salts; polymerization by products; moisture | Balance to 100 |

Thirty-five pounds of this polyglycerol are added to a stainless steel reactor equipped with mechanical agitating device, electric heating device, and nitrogen sparging. 23.3 pounds of food-grade stearic acid are added, whereafter, the reaction is heated under agitation to a temperature of about 460°F (about 238°C). The esterification is carried out under a pressure of about 11 inches mercury. When the free fatty acid content drops below 2 percent, the esterification product is deodorized under an absolute pressure of 6 millimeter mercury for about one hour under agitation and nitrogen sparging. The reaction product contains 0.1% free fatty acid and is a polyglycerol fatty acid ester emulsifier useful for a wide range of food applications inclusive of cake baking, pie crust, salad dressing and frying. Thirty-five percent of the hydroxyl groups of the polyglycerol are reacted.

What is claimed is:

1. A process for preparing linear polyglycerol comprising:
    a. heating glycerol to a temperature in the range from about 110° to about 180°C at a pressure below about 400 mm absolute mercury pressure in the presence of from about 0.03 to about 3% by weight sulfuric acid; and from about 0.1 to about 10% by weight of a glyceride compound having the formula

wherein $R_1$ represents $CH_3-$, or $CH_3CH_2-$; and $n$ represents an integer from 1 to 3 inclusive; until from about 25 to about 75 percent of the glycerol is polymerized;
    b. inactivating said sulfuric acid by the addition of a substantially stoichiometric amount of a neutralizing agent; and
    c. removing the unreacted glycerol by distillation.

2. A process in accordance with claim 1 wherein said sulfuric acid is present in an amount of from about 0.08 to about 0.3% by weight and wherein said glyceride is present in an amount of from about 0.5 to about 5% by weight.

3. A process in accordance with claim 2 wherein from about 35 to about 60 percent of said glycerol is polymerized.

4. A process in accordance with claim 3 wherein said glycerol is heated to a temperature in the range of from about 120°C to about 145°C at from about 1 to about 20 mm absolute mercury pressure.

5. A process in accordance with claim 4 wherein said neutralizing agent is an alkali metal or alkaline earth metal hydroxide, carbonate or bicarbonate.

6. A process in accordance with claim 5 wherein said glyceride is mono-, di-, or triacetin.

7. A process for preparing linear polyglycerol comprising:
    a. heating glycerol to a temperature in the range of from about 120°C to about 145°C at an absolute mercury pressure of from about 1 mm to about 20 mm in the presence of from about 0.08 to about 0.3% by weight of sulfuric acid; and of from about 0.5 to about 5% by weight of mono-, di-, or triacetin; until of from about 35 to about 60 percent of said glycerol is polymerized;
    b. inactivating said sulfuric acid by the addition of a substantially stoichiometric amount of a neutralizing agent; and
    c. removing the unreacted glycerol by distillation.

* * * * *